(12) United States Patent
Brown et al.

(10) Patent No.: US 10,928,345 B2
(45) Date of Patent: Feb. 23, 2021

(54) IN-SENSOR SPAN CALIBRATION FOR MEMS OZONE SENSOR

(71) Applicant: Apple Inc., Cupertino, CA (US)

(72) Inventors: Michael K. Brown, Sunnyvale, CA (US); Miaolei Yan, Santa Clara, CA (US); Roberto M. Ribeiro, San Jose, CA (US)

(73) Assignee: Apple Inc., Cupertino, CA (US)

( * ) Notice: Subject to any disclaimer, the term of this patent is extended or adjusted under 35 U.S.C. 154(b) by 190 days.

(21) Appl. No.: 16/276,460

(22) Filed: Feb. 14, 2019

(65) Prior Publication Data

US 2019/0265183 A1 Aug. 29, 2019

Related U.S. Application Data

(60) Provisional application No. 62/636,796, filed on Feb. 28, 2018.

(51) Int. Cl.
*G01N 27/00* (2006.01)
*G01N 27/12* (2006.01)
*G01N 33/00* (2006.01)

(52) U.S. Cl.
CPC ......... *G01N 27/123* (2013.01); *G01N 27/125* (2013.01); *G01N 33/0006* (2013.01); *G01N 33/0039* (2013.01)

(58) Field of Classification Search
CPC ............... G01N 27/123; G01N 27/125; G01N 33/0006; G01N 33/0039
See application file for complete search history.

(56) References Cited

U.S. PATENT DOCUMENTS

| | | | |
|---|---|---|---|
| 9,817,445 B1 * | 11/2017 | Greene, Jr. | G01J 5/0265 |
| 2012/0297868 A1 * | 11/2012 | Elkins | E21B 47/06 |
| | | | 73/152.31 |
| 2019/0060821 A1 * | 2/2019 | Mou | F04B 39/121 |
| 2019/0194013 A1 * | 6/2019 | Chandrasekaran | H04R 19/04 |
| 2019/0195785 A1 * | 6/2019 | Goda | G01N 21/274 |
| 2019/0257803 A1 * | 8/2019 | Brown | G01N 33/0031 |
| 2020/0237947 A1 * | 7/2020 | Brown | A61L 9/20 |

* cited by examiner

*Primary Examiner* — Jamel E Williams
(74) *Attorney, Agent, or Firm* — Morgan, Lewis & Bockius LLP

(57) ABSTRACT

A portable communication device may include a gas sensor enclosed in an enclosure, a port to allow flow of air into and out of the enclosure, and a light source disposed on an internal surface of the enclosure. The light source is operable to facilitate generation of ozone gas within the enclosure. The enclosure may contain a heating element that allows baseline calibration of the gas sensor by thermally decomposing ozone gas molecules. The gas sensor includes a miniature gas sensor such as a metal-oxide (MOX) gas sensor.

20 Claims, 4 Drawing Sheets

| | Step 1 | Step 2 | Step 3 |
|---|---|---|---|
| Heating Element | On-High | On-High, On-Low, or off | On-High, On-Low, or off |
| UV Emitter | Off | On | Off |
| MOX Sensor | Baseline Reading | Reading $O_3$ | Reading $O_3$ |
| Air Pump | On -> Off (or) Off | Off | Off |

IN-SENSOR SPAN CALIBRATION FOR MEMS OZONE SENSOR

CROSS-REFERENCE TO RELATED APPLICATIONS

The present application claims the benefit of U.S. Provisional Patent Application Ser. No. 62/636,796, entitled "IN-SENSOR SPAN CALIBRATION FOR MEMS OZONE SENSOR," filed on Feb. 28, 2018, which is hereby incorporated by reference in its entirety for all purposes.

TECHNICAL FIELD

The present description relates generally to transducers, and more particularly, to an in-sensor span calibration for micro electro-mechanical system (MEMS) ozone sensor.

BACKGROUND

Miniature gas sensors for consumer electronics represent a technology category that could enable upcoming features and/or products in applications such as, e.g., environmental and health monitoring, smart homes, and internet of things (IoT). Metal oxide (MOX) gas sensors are among the most promising technologies to be integrated with consumer electronic devices due to their small size, low power consumption, compatibility with semiconductor fabrication processes, and relatively simple architecture. Chemical poisoning and deactivation of the sensor materials in metal oxide sensors, however, can cause drift in both baseline resistance and sensitivity, which can pose great challenges to the mass market adoption of miniature gas sensors.

Many MOX gas sensors consist of a porous MOX material dispensed on a micro-hotplate, which is used to regulate temperature. When heated to the working temperature, the resistance of the metal oxide material changes with the gas environment and concentration. The target gas can be an oxidizing gas such as ozone ($O_3$) or nitrogen oxide ($NO_x$), which increases MOX resistance. The target gas may be a reducing gas, for example, hydrogen ($H_2$) or volatile organic compounds (VOC), which decreases the MOX resistance. Most MOX film gas sensors are intrinsically susceptible to calibration drift, both baseline and sensitivity (span) drift. Various techniques can be employed to detect and mitigate calibration drift, for example, by modeling sensor behavior over time and periodically co-locating the sensor with reference instrumentation to facilitate calibration of the sensor. These techniques, however, may not often be practical or economical solutions.

Depending on the gas species of interest, a zero-target-gas condition can be created with the use of heat or scrubbing. Span calibration points may require exposing the sensor to known levels of target gas, which may not be practical without substantial generation and/or reference equipment. It is understood that many target gases cannot be generated or quantified in a controllable, miniaturized, or intrinsically safe manner.

BRIEF DESCRIPTION OF THE DRAWINGS

Certain features of the subject technology are set forth in the appended claims. However, for purposes of explanation, several embodiments of the subject technology are set forth in the following figures.

DETAILED DESCRIPTION

The detailed description set forth below is intended as a description of various configurations of the subject technology and is not intended to represent the only configurations in which the subject technology may be practiced. The appended drawings are incorporated herein and constitute a part of the detailed description. The detailed description includes specific details for the purpose of providing a thorough understanding of the subject technology. However, the subject technology is not limited to the specific details set forth herein and may be practiced without one or more of the specific details. In some instances, structures and components are shown in block diagram form in order to avoid obscuring the concepts of the subject technology.

In one or more aspects, the subject technology is directed to devices and configurations for an in-sensor span calibration of a micro electro-mechanical system (MEMS) ozone (03) sensor. The subject technology leverages a light source to generate ozone gas from the air inside a gas-sensing device. Ozone gas can be generated using short wavelength ultraviolet (UV) light (e.g., ~185 nm) or with corona discharge. Short wavelength UV light can split O2 molecules into two oxygen free radicals (O). The free radicals can readily combine with O2 molecules to create ozone gas molecules (O+O2=O3).

The disclosed solution is to integrate a controllable UV light source within an enclosure of a gas-sensing device along with a sensor, selective to ozone gas, including a metal-oxide (MOX) or an electrochemical ozone gas sensor or another ozone gas sensor. The UV light source can be activated, for example, periodically to produce small quantities of ozone gas, which would be used as span calibration point(s) for the MOX sensor. The level of ozone gas generated may be dependent on a number of conditions such as the sensor geometry, ambient air temperature, relative humidity, barometric pressure and presence of ozone and/or cross sensitive gases and/or other factors. These conditions can be detected with co-located sensors, or be modeled based upon multiple parameters such as location, time of day, weather condition and the like.

The drive scheme of the UV light source can be a periodic or pulse-width modulated (PWM) scheme, and the intensity and duration of the UV source can be varied to provide various span calibration levels. In situations where the carrier (ambient) gas cannot be treated to reach a near zero-level of ozone, the in-sensor ozone gas generation technique could still be utilized to increase the level of ozone gas to create a specified ozone concentration delta. This would allow achieving an effective span calibration of the ozone gas.

Figures 1, 2:
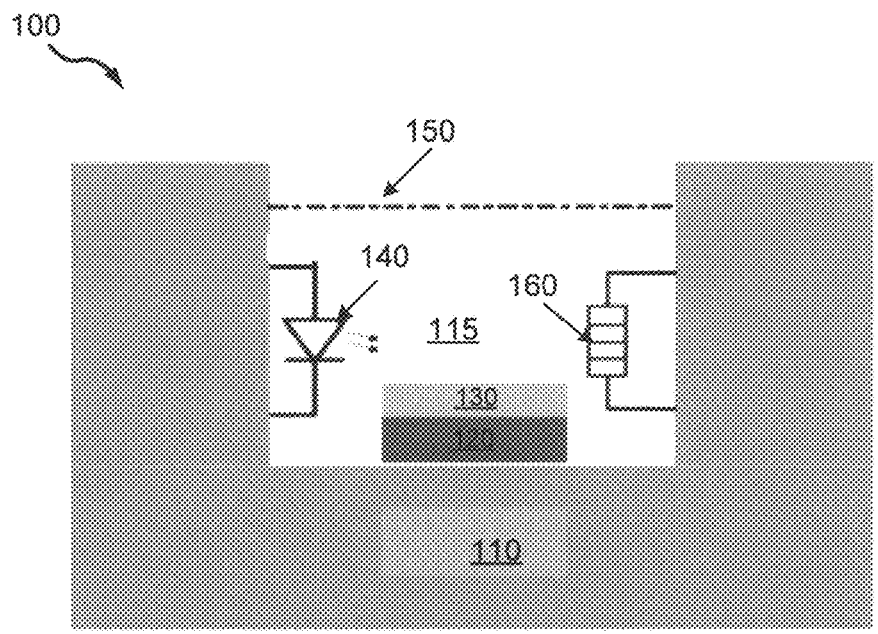
FIG. 1 is a schematic diagram illustrating an example of a miniature gas-sensing device capable of in-sensor span calibration, in accordance with one or more aspects of the subject technology.
FIG. 2 is a table illustrating example stages of the in-sensor span calibration of the miniature gas-sensing device of FIG. 1, in accordance with one or more aspects of the subject technology.

FIG. 1 is a schematic diagram illustrating an example of a miniature gas-sensing device 100 capable of in-sensor span calibration, in accordance with one or more aspects of the subject technology. The miniature gas-sensing device (hereinafter "gas-sensing device") 100 can be integrated with a host device such as a consumer electronic device, for example, a portable communication device (e.g., a smart phone or a smart watch). The gas-sensing device 100 includes an enclosure 110, a hotplate 120, a gas sensor 130, a light source 140, a port 150 and a heating element 160. The port 150 allows diffusion of air in and out of a cavity 115 of the miniature gas-sensing device 100. Ozone gas can be generated by interaction of the short wavelength UV light (e.g., ~185 nm) generated by the light source 140 with the oxygen content of the air inside the cavity 115. The gas sensor 130 is sensitive to the ozone gas and, in some implementations, can be a MOX or an electrochemical gas sensor, but is not limited to these gas sensors and can be made of other appropriate gas sensitive materials suitable for sensing ozone. The underlying principle of MOX gas sensors are based on chemisorption of oxidizing or reducing gas species on the oxide surface, which is followed by a charge transfer process that can result in resistance changes of the MOX material. Examples of metal oxide materials include, but are not limited to, tin oxide ($SnO_2$), indium oxide ($In_2O_3$), tungsten oxide ($WO_3$), zinc oxide (ZnO), or a mixture thereof.

In some implementations, the light source 140 can be a light emitting diode (LED) disposed on an internal surface (e.g., a wall) of the enclosure 110. The light source 140 can generate short wavelength UV light that can facilitate generating ozone gas from the oxygen content of the air inside the cavity 115. A sensitive surface of gas sensor 130 has to be shielded from the UV light of the light source 140 to prevent formation of cross sensitive signals. The shielding of the gas sensor 130 can be achieved by geometric configuration and proper alignment such that there is not a direct light path between the light source 140 and the gas sensor 130. In some implementations, the location of the light source 140 is chosen to prevent the sensitive surface of gas sensor 130 from being exposed to UV light generated by the light source 140.

In some implementations, the hotplate 120 is a micro electromechanical system (MEMS) hotplate and can include titanium nitride, which is compatible with complementary metal-oxide semiconductor (CMOS) process and has a high melting point (e.g., 2950° C.), although other suitable metals may be used. In some implementations, the hotplate 120 can be controlled (e.g., by a microcontroller or a general processor) and may be used to regulate the temperature of the gas sensor 130. In some implementations, the hotplate 120 may be configured to provide sufficient thermal energy to eliminate the need for the heating element 160.

In one or more implementations, the miniature gas-sensing device 100 can be integrated with a host device such as a consumer electronic device, for example, a portable communication device (e.g., a smart phone or a smart watch). In some implementations, a driver of the light source 140 can be controlled by a processor or a processing module of the host device. For example, the processor or the processing module may cause the driver of the light source 140 to generate periodic pulses with varying amplitude and duration. In some aspects, the generated periodic pulses can be PWM pulses. In one or more implementations, the processor or the processing module of the host device can control the temperature of the heating element 160, for example, to make the environment inside the cavity 115 hot enough (e.g., above 50° C.) to thermally decompose the ozone gas. This would facilitate baseline calibration (at nearly zero ozone concentration) of the sensor. The processor or the processing module of the host device can also be used to turn the heating element 160 off or low or to turn it up to reach a desired temperature range, as needed.

In some implementations, the material for the enclosure 110 may be a metal such as aluminum, stainless steel or other metals or metallic alloys or other suitable materials. The port 150 may be an air permeable membrane made of a porous material, which can be waterproof to protect the sensors against moisture and humidity.

FIG. 2 is a Table 200 illustrating example stages of the in-sensor span calibration of the miniature gas-sensing device 100 of FIG. 1, in accordance with one or more aspects of the subject technology. For in-sensor span calibration of the miniature gas-sensing device 100, the light source 140 (e.g., UV emitter) is used to generate ozone from the oxygen content of the cavity 115 of FIG. 1, as described above. Further, the heating element 160 can be used to achieve baseline calibration (e.g., near zero ozone concentration) by thermally decomposing the ozone gas content of the cavity 115. Table 200 includes three columns (1 to 3), each of which represents a stage of the calibration process of the gas sensor (e.g., 130 of FIG. 1).

The first stage is for baseline calibration of the gas sensor 130 of the miniature gas-sensing device 100. For the first stage, the hotplate 120 is set to a high temperature (e.g., above 50° C., also referred to as "hot") by the calibration processor (e.g., of the host device) to reset the MOX sensor 130 to a known state. In some implementations, the heating element 160 is set to the high temperature to decompose the existing ozone gas content of the cavity 115 to reach a near zero concentration of the ozone gas. At this stage, a resistance value of the gas sensor 130 is read and stored as the baseline value. For this stage, as shown in column 1 of Table 200, the light source 140 (UV emitter) is off, so no generation of the ozone gas by the UV emitter is taking place.

The second stage is for reading a current value of the gas sensor 130 representing the current concentration of ozone gas in the cavity, while the ozone gas is being generated by the light source 140 that is turned on, as shown in column 2 of Table 200. In this stage, the heating element 160 is turned off or set to a lower temperature and the light source 140 is turned on by the calibration processor of the host device. The reduction in heating element temperature can reduce the rate of thermal decomposition of the ozone gas, while the ozone gas is being generated by the UV light of the light source 140. Further, an anticipated ozone gas concentration can be modeled based upon a number of factors such as geometry of the gas-sensing device 100, diffusion characteristics of the port 150, oxygen level (e.g., determined based upon location and/or barometric pressure), relative humidity level, and drive scheme (e.g., level and/or duration) of the UV light source.

The third stage is the reading stage where the resistance value of the gas sensor 130 is captured while the heating element 160 is turned off or turned low. Further, the light source 140 is turned off, by the calibration processor of the host device, to prevent thermal decomposition of the ozone gas, thus no ozone gas is being generated. This stage is the routine ozone gas detection and measurement by the gas-sensing device 100, where the measured resistance of the gas sensor 130 is stored in a memory of the host device. In some implementations, the rate of decay of ozone detected by the gas sensor 130 can be used in the establishment of the sensor calibration.

In some implementations, co-located sensor measurement data and or other data such as location data (e.g., indoor and/or outdoor/elevation), barometric pressure (e.g., air density) sensor data, temperature and/or relative humidity (RH) sensor data, VOC sensor data, acceleration and/or gyro (e.g., static movement) data can be used for establishing an estimated target gas generation level.

Figures 3, 4:
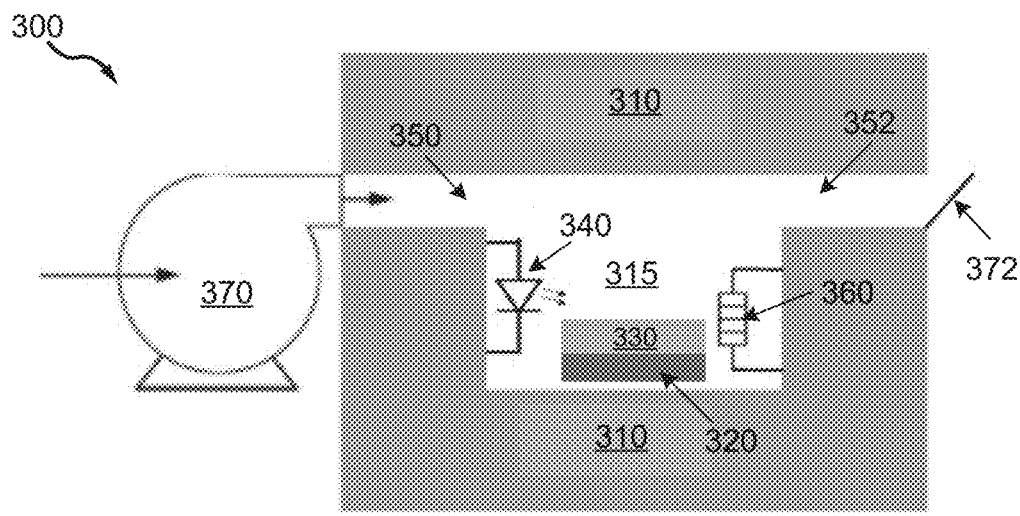
FIG. 3 is a schematic diagram illustrating an example of a miniature gas-sensing device capable of in-sensor span calibration, in accordance with one or more aspects of the subject technology.
FIG. 4 is a table illustrating example stages of the in-sensor span calibration of the miniature gas-sensing device of FIG. 3, in accordance with one or more aspects of the subject technology.

FIG. 3 is a schematic diagram illustrating an example of a miniature gas-sensing device 300 capable of in-sensor span calibration, in accordance with one or more aspects of the subject technology. The miniature gas-sensing device 300 (hereinafter "gas-sensing device 300") can be integrated with a host device such as a consumer electronic device, for example, a portable communication device (e.g., a smart phone or a smart watch). The gas-sensing device 300 includes an enclosure 310, a hotplate 320, a gas sensor 330, a light source 340, an input port 350, an exit port 352 and a heating element 360. In some implementations, the input port 350 includes an air blower 370 that can blow the air into a cavity 315 of the gas-sensing device 300, and the exit port 352 may include a valve 372. The air blower 370 may be a mechanical pump, a piezo pump or a speaker of a host device. The air blower 370 is primarily used for gas sensor 330 operation, and optionally may not be used during calibration. In one or more implementations, the valve 372 can be a one-way valve that only allows air to exit from a cavity 315 of the gas-sensing device 300. The air blower 370 and the valve 372 may be controlled by a processor (e.g., a microcontroller or a general-purpose processor) such as a processor of the host device. In some implementations, the blower 360 may be located on the exhaust port downstream of the sensor element 330; a valve 372 may be located on the inlet port. The air blower 370 and the valve 372 may be used to establish a known sample or continual velocity of air flow in the cavity 315. The light source 340 emits short wavelength UV light (e.g., ~185 nm) that can generate ozone gas by interaction of the short wavelength UV light with the oxygen content of the air inside the cavity 315. The hotplate 320, the gas sensor 330, the light source 340, and the heating element 360 are similar to the hotplate 120, the gas sensor 130, light source 140, and the heating element 160 of FIG. 1 described above. The enclosure 310 can be made of a metal such as aluminum, stainless steel or other metals or metallic alloys or other suitable materials. In some implementations, the light source 340 can be a light emitting diode (LED) disposed on an internal surface (e.g., a wall) of the enclosure 310. In order to prevent formation of cross sensitive signals, a sensitive surface of the gas sensor 330 is shielded from being impinged upon by the UV light of the light source 340 by geometric configuration and proper alignment as discussed above.

In some implementations, a driver of the light source 340 can be controlled by a processor or a processing module of the host device, for example, to generate periodic drive signals with varying amplitude and duration or PWM pulses. In one or more implementations, the processor or the processing module of the host device can control the temperature of the heating element 360, for example, to increase the temperature of the ozone gas inside the cavity 315 to a sufficiently high level (e.g., above 50° C.) to be able to thermally break down ozone molecules. This would allow baseline calibration (at nearly zero ozone concentration) of the gas sensor 330. The heating element 360 can also be turned off or low or turned up, by the processor or the processing module of the host device, to reach a desired temperature range, as needed.

FIG. 4 is a Table 400 illustrating example stages of the in-sensor span calibration of the miniature gas-sensing device 300 of FIG. 3, in accordance with one or more aspects of the subject technology. For in-sensor span calibration of the gas-sensing device 300 the light source 340 (e.g., UV emitter) is used to generate ozone from the oxygen content of the cavity 315 of FIG. 3, as described above. Further, the heating element 360 can be used to achieve baseline calibration (e.g., near zero ozone concentration) by thermally decomposing the ozone gas content of the cavity 315. Table 400 includes three columns (1 to 3), each of which represents a stage of the gas sensor (e.g., 330 of FIG. 1) calibration process.

The first stage is for baseline calibration of the gas sensor 130 of the miniature gas-sensing device 100 (gas sensor). In the first stage, the hotplate 320 is set to be hot by the calibration processor (e.g., of the host device) reset the MOX sensor 130 to a known state. The heating element 360 is set to a high temperature to decompose the existing ozone gas content of the cavity 315 to reach a near zero concentration of the ozone gas. At this stage a resistance value of the gas sensor 330 (gas sensor) is read and stored as the baseline value. For this stage, as shown in column 1 of Table 400, the light source 340 (UV emitter) is off, and thus no generation of the ozone gas by the UV emitter is taking place, and the air blower 370 pumps fresh air into cavity 315. The air blower 370 may be turned off in the middle of the first stage to allow all ozone to be consumed by the thermal breakdown (decomposition) process caused the heating element 360. Optionally the air blower 370 may be off throughout the calibration process.

The second stage is for reading a current value of the resistance of the gas sensor 330 representing the current concentration of ozone gas in the cavity, while the ozone gas is being generated by the light source 340 that is turned on, as shown in column 2 of Table 400. In this stage, the heating element 360 is turned off or turned low set to a lower temperature and the light source 340 is turned on by the calibration processor of the host device. The reduction in heating element temperature can reduce the rate of thermal decomposition of the ozone gas, while the ozone gas is being generated by the UV light of the light source 340. With the air blower 370 off, the light source 340 operates at either PWM or timed output consuming oxygen and generating a known quantity of ozone gas. The known quantity of ozone gas is based upon the determined level of oxygen in the cavity 315 (e.g., determined based upon location and/or barometric pressure) and UV emission intensity and/or duration of the known quantity of ozone gas. The air blower 370 may be turned on during this stage to allow modulation of the level of generated ozone gas based upon the rate of flow and the level of UV light intensity.

During a third stage, as shown in column 3 of Table 400, the heating element 360 remains off or at the low temperature, while the light source 340 is still off. This stage is for ozone gas detection and measurement by the gas-sensing device 300, where the resistance of the gas sensor 330 is captured at various time instances during or after the ozone generation event, and stored in a memory of the host device. In some implementations, the rate of decay of ozone detected by the gas sensor 330 can be used in the establishment of the sensor calibration.

Again, the anticipated ozone gas concentration can be modeled based upon a number of factors such as the geometry of the gas-sensing device 300, the drive scheme characteristics of the air blower 370, the determined oxygen level, the relative humidity level, and the drive scheme (e.g., level and/or duration) of the UV light source 340. In some implementations, co-located sensor measurement data and or other data such as location data (e.g., indoor and/or outdoor and/or elevation), barometric pressure (e.g., air density) sensor data, temperature and/or relative humidity (RH) sensor data, VOC sensor data, acceleration and/or gyro sensor data can be used for establishing an estimated target gas generation level. In one or more implementations, the intensity level and/or duration of the zero level and ozone generation pulses can be varied to establish multiple effective levels of ozone gas. The frequency of the in-sensor calibration can be modulated based upon the anticipated sensor drift, incidence of suitable calibration parameters and other factors.

Figure 5:
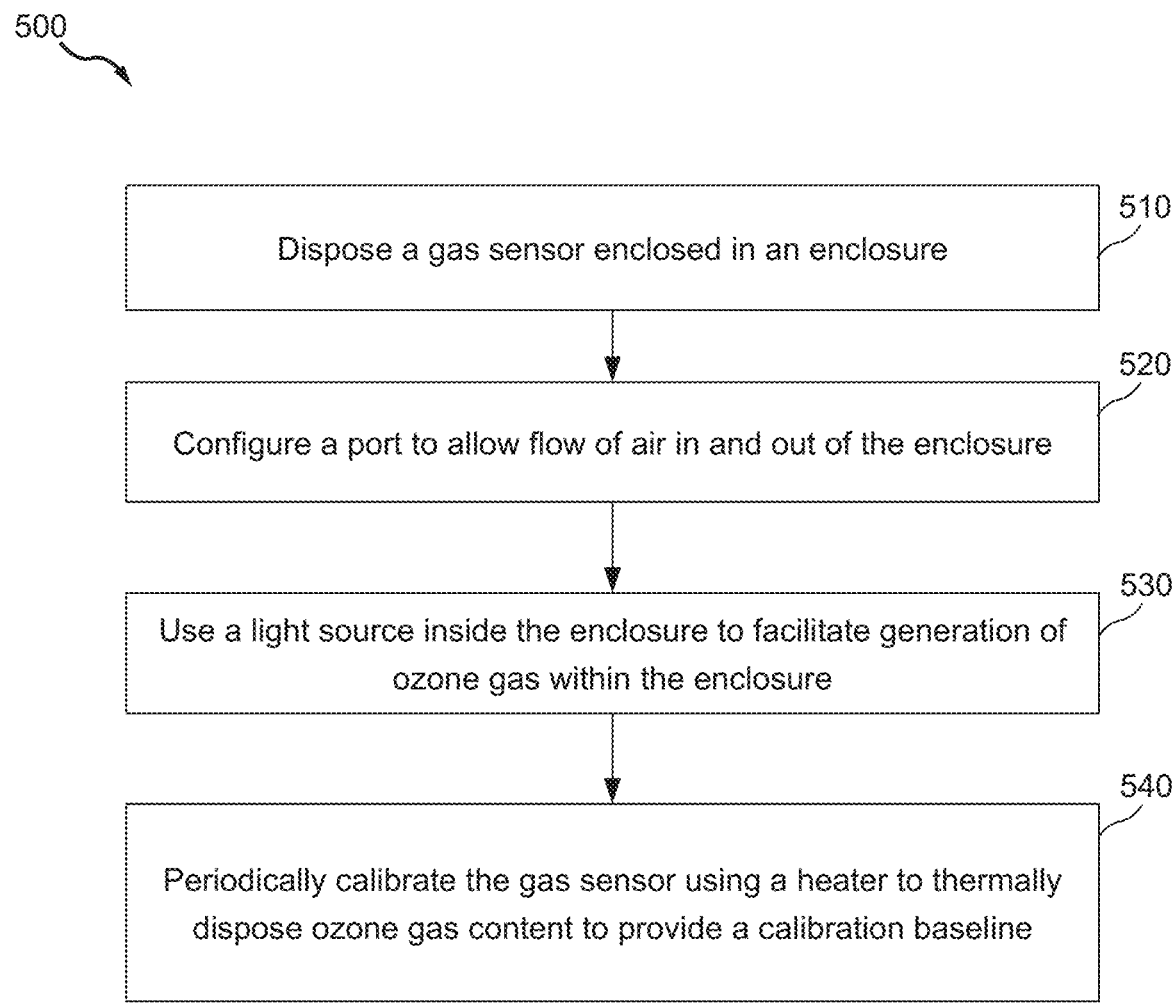
FIG. 5 is a flow diagram illustrating an example method of providing of a miniature gas-sensing device capable of in-sensor span calibration, in accordance with one or more aspects of the subject technology.

FIG. 5 is a flow diagram illustrating an example method 500 of providing of a miniature gas-sensing device (e.g., 100 of FIG. 1) capable of in-sensor span calibration, in accordance with one or more aspects of the subject technology. The method 500 starts with providing a gas sensor (e.g., 130 of FIG. 1) enclosed in an enclosure (e.g., 110 of FIG. 1) (510). A port (e.g., 150 of FIG. 1) may be configured to allow flow of air in and out of the enclosure (520). A light source (e.g., 140 of FIG. 1) inside the enclosure may be used to facilitate generation of ozone gas within the enclosure (530). The gas sensor is periodically calibrated, in some implementations using a heating element (e.g., 160 of FIG. 1) to thermally dispose ozone gas content to provide a calibration baseline (540).

Figure 6:
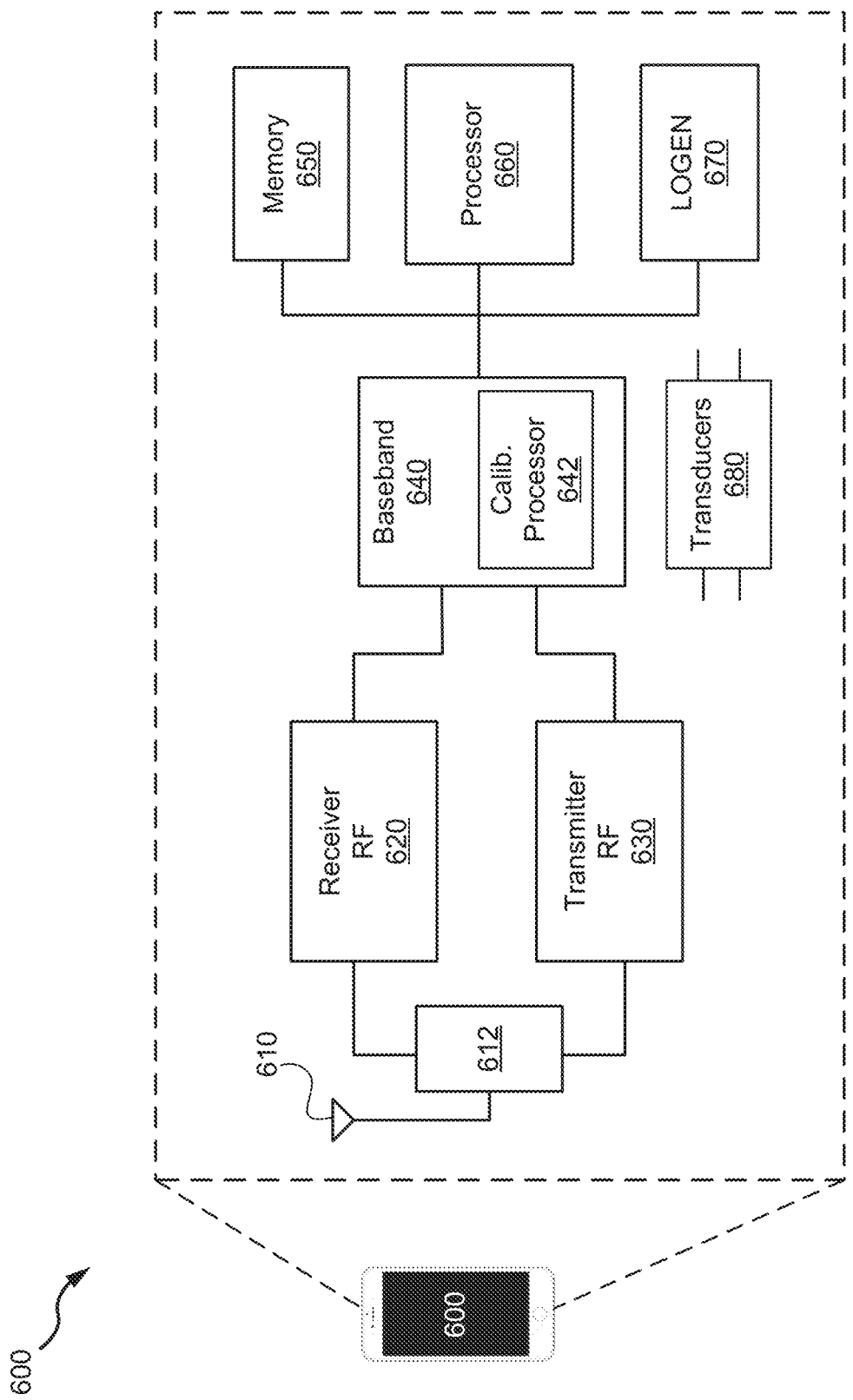
FIG. 6 is a block diagram illustrating an example wireless communication device, within which one or more miniature gas sensors of the subject technology can be integrated.

FIG. 6 is a block diagram illustrating an example wireless communication device 600, within which one or more miniature gas sensors of the subject technology can be integrated. The wireless communication device 600 may be the host device of the gas-sensing devices (e.g., 100 of FIG. 1 or 300 of FIG. 3) of the subject technology. The wireless communication device 600 may comprise a radio-frequency (RF) antenna 610, a receiver 620, a transmitter 630, a baseband processing module 640, a memory 650, a processor 660, a local oscillator generator (LOGEN) 670 and one or more transducers 680. In various embodiments of the subject technology, one or more of the blocks represented in FIG. 6 may be integrated on one or more semiconductor substrates. For example, the blocks 620-670 may be realized in a single chip or a single system on a chip, or may be realized in a multi-chip chipset.

The receiver 620 may comprise suitable logic circuitry and/or code that may be operable to receive and process signals from the RF antenna 610. The receiver 620 may, for example, be operable to amplify and/or down-convert received wireless signals. In various embodiments of the subject technology, the receiver 620 may be operable to cancel noise in received signals and may be linear over a wide range of frequencies. In this manner, the receiver 620 may be suitable for receiving signals in accordance with a variety of wireless standards, Wi-Fi, WiMAX, Bluetooth, and various cellular standards. In various embodiments of the subject technology, the receiver 620 may not require any SAW filters and few or no off-chip discrete components such as large capacitors and inductors.

The transmitter 630 may comprise suitable logic circuitry and/or code that may be operable to process and transmit signals from the RF antenna 610. The transmitter 630 may, for example, be operable to up-convert baseband signals to RF signals and amplify RF signals. In various embodiments of the subject technology, the transmitter 630 may be operable to up-convert and amplify baseband signals processed in accordance with a variety of wireless standards. Examples of such standards may include Wi-Fi, WiMAX, Bluetooth, and various cellular standards. In various embodiments of the subject technology, the transmitter 630 may be operable to provide signals for further amplification by one or more power amplifiers.

The duplexer 612 may provide isolation in the transmit band to avoid saturation of the receiver 620 or damaging parts of the receiver 620, and to relax one or more design requirements of the receiver 620. Furthermore, the duplexer 612 may attenuate the noise in the receive band. The duplexer may be operable in multiple frequency bands of various wireless standards.

The baseband processing module 640 may comprise suitable logic, circuitry, interfaces, and/or code that may be operable to perform processing of baseband signals. The baseband processing module 640 may, for example, analyze received signals and generate control and/or feedback signals for configuring various components of the wireless communication device 600, such as the receiver 620. The baseband processing module 640 may be operable to encode, decode, transcode, modulate, demodulate, encrypt, decrypt, scramble, descramble, and/or otherwise process data in accordance with one or more wireless standards.

In some implementations, the baseband processing module 640 may include a calibration processor 642 that is capable of controlling calibration of the miniature gas sensor of the subject technology.

The processor 660 may comprise suitable logic, circuitry, and/or code that may enable processing data and/or controlling operations of the wireless communication device 600. In this regard, the processor 660 may be enabled to provide control signals to various other portions of the wireless communication device 600. The processor 660 may also control transfers of data between various portions of the wireless communication device 600. Additionally, the processor 660 may enable implementation of an operating system or otherwise execute code to manage operations of the wireless communication device 600. In one or more implementations, the processor 660 may be configured to control calibration of the miniature gas sensor of the subject technology.

The memory 650 may comprise suitable logic, circuitry, and/or code that may enable storage of various types of information such as received data, generated data, code, and/or configuration information. The memory 650 may comprise, for example, RAM, ROM, flash, and/or magnetic storage. In various embodiment of the subject technology, information stored in the memory 650 may be utilized for configuring the receiver 620 and/or the baseband processing module 640.

The local oscillator generator (LOGEN) 670 may comprise suitable logic, circuitry, interfaces, and/or code that may be operable to generate one or more oscillating signals of one or more frequencies. The LOGEN 670 may be operable to generate digital and/or analog signals. In this manner, the LOGEN 670 may be operable to generate one or more clock signals and/or sinusoidal signals. Characteristics of the oscillating signals such as the frequency and duty cycle may be determined based on one or more control signals from, for example, the processor 660 and/or the baseband processing module 640.

In operation, the processor 660 may configure the various components of the wireless communication device 600 based on a wireless standard according to which it is desired to receive signals. Wireless signals may be received via the RF antenna 610 and amplified and down-converted by the receiver 620. The baseband processing module 640 may perform noise estimation and/or noise cancellation, decoding, and/or demodulation of the baseband signals. In this manner, information in the received signal may be recovered and utilized appropriately. For example, the information may be audio and/or video to be presented to a user of the wireless communication device, data to be stored to the memory 650, and/or information affecting and/or enabling operation of the wireless communication device 600. The baseband processing module 640 may modulate, encode, and perform other processing on audio, video, and/or control signals to be transmitted by the transmitter 630 in accordance with various wireless standards.

The one or more transducers 680 may include the miniature has sensor of the subject technology as shown in FIGS. 1 and 3 and described above. The miniature has sensor of the subject technology can be readily integrated into the wireless communication device 600, in particular when the wireless communication device 600 is a smart mobile phone or a smart watch.

The previous description is provided to enable any person skilled in the art to practice the various aspects described herein. Various modifications to these aspects will be readily apparent to those skilled in the art, and the generic principles defined herein may be applied to other aspects. Thus, the claims are not intended to be limited to the aspects shown herein, but are to be accorded the full scope consistent with the language claims, wherein reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the subject disclosure.

The predicate words "configured to", "operable to", and "programmed to" do not imply any particular tangible or intangible modification of a subject, but, rather, are intended to be used interchangeably. For example, a processor configured to monitor and control an operation or a component may also mean the processor being programmed to monitor and control the operation or the processor being operable to monitor and control the operation. Likewise, a processor configured to execute code can be construed as a processor programmed to execute code or operable to execute code.

A phrase such as an "aspect" does not imply that such aspect is essential to the subject technology or that such aspect applies to all configurations of the subject technology. A disclosure relating to an aspect may apply to all configurations, or one or more configurations. A phrase such as an aspect may refer to one or more aspects and vice versa. A phrase such as a "configuration" does not imply that such configuration is essential to the subject technology or that such configuration applies to all configurations of the subject technology. A disclosure relating to a configuration may apply to all configurations, or one or more configurations. A phrase such as a configuration may refer to one or more configurations and vice versa.

The word "example" is used herein to mean "serving as an example or illustration." Any aspect or design described herein as "example" is not necessarily to be construed as preferred or advantageous over other aspects or designs. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for." Furthermore, to the extent that the term "include," "have," or the like is used in the description or the claims, such term is intended to be inclusive in a manner similar to the term "comprise" as "comprise" is interpreted when employed as a transitional word in a claim.

What is claimed is:

1. A portable communication device, the device comprising:
    a gas sensor enclosed in an enclosure;
    a port configured to allow flow of air into and out of the enclosure;
    a light source disposed on an internal surface of the enclosure and operable to facilitate generation of ozone gas within the enclosure; and
    a heating element configured to heat the air within the enclosure to reduce or eliminate a presence of ozone gas.

2. The device of claim 1, wherein the gas sensor comprises a miniature gas sensor based on a metal-oxide (MOX).

3. The device of claim 1, wherein the light source comprises a short-wavelength ultra-violet (UV) light source and is configured to facilitate generating various levels of ozone gas based on oxygen content of air inside the enclosure.

4. The device of claim 3, wherein the light source is controlled to allow in-sensor span calibration of the gas sensor based on the generated various levels of ozone gas.

5. The device of claim 4, further comprising a calibration processor configured to control periodic performance of the in-sensor span calibration.

6. The device of claim 5, wherein the calibration processor is configured to control the periodic performance of the in-sensor span calibration independent of a location of the device.

7. The device of claim 1, wherein the port includes an air-permeable membrane, wherein the air-permeable membrane is made of a porous material.

8. The device of claim 1, wherein the port comprises an input port including a one-way valve or an air blower, wherein the air blower comprises a mechanical pump, a piezo pump or a speaker of the device.

9. The device of claim 8, further comprising an exit port including an air blower or a one-way valve configured to allow adjusting ozone gas content of the enclosure by controlling a flow of air exiting the enclosure.

10. The device of claim 1, wherein a geometric location of the light source inside the enclosure is configured to prevent light rays from impinging upon a sensitive surface of the gas sensor.

11. The device of claim 1, wherein the light source is driven using a pulse-with modulated signal or a periodic signal with controllable duty cycle, and wherein an intensity of the light source is controllable.

12. The device of claim 1, wherein the heating element is configured to generate heat to decompose ozone gas content of the enclosure to facilitate baseline calibration of the ozone gas at approximately zero ozone gas concentration.

13. A device comprising:
an enclosure including at least one port;
a gas sensor enclosed in the enclosure; and
a light source disposed on an internal surface of the enclosure and configured to enable generation of ozone gas from an air inside the enclosure,
wherein the at least one port is configured to allow an air flow in and out of the enclosure.

14. The device of claim 13, wherein the light source is configured to enable generation of various levels of ozone gas based on an intensity and timing of the light source controlled by a driver signal of the light source, wherein the driver signal of the light source is one of a periodic signal or a pulse-width modulated signal, wherein the gas sensor is configured to measure a rate of decay of the ozone gas, and wherein the measured rate of decay of the ozone gas is useable for gas sensor calibration.

15. The device of claim 13, and wherein the heating element is configured to allow baseline calibration of the gas sensor by thermal decomposition of the ozone gas to reach a level of approximately zero ozone concentration.

16. The device of claim 13, wherein the at least one port comprises an air-permeable membrane or an input port and an exit port, wherein the input port includes an air blower and the exit port includes a one-way valve or the input port includes a one-way valve and the exit port includes an air blower.

17. The device of claim 16, wherein the air blower and the one-way valve are configured to control a flow level of sample gas in the enclosure.

18. A system comprising:
a communication device; and
a miniature gas sensor integrated with the communication device,
wherein the miniature gas sensor is disposed on a hotplate enclosed in an enclosure, the enclosure further includes at least one port, a light source disposed on an internal surface of the enclosure the enclosure and is configured to facilitate generation of various levels of ozone gas, and a heating element configured to permit baseline calibration of the miniature gas sensor.

19. The system of claim 18, wherein the miniature gas sensor comprises a metal-oxide (MOX)-based gas sensor, and wherein the light source comprises a short-wavelength ultra-violet (UV) light source driven by a periodic pulse or a pulse-width modulated signal.

20. The system of claim 18, wherein the heating element is configured to generate heat to decompose ozone gas content of the enclosure to facilitate base line calibration of the ozone gas at approximately zero ozone gas concentration.

* * * * *